(12) United States Patent
Shenouda

(10) Patent No.: US 11,549,933 B2
(45) Date of Patent: Jan. 10, 2023

(54) MAGNETIC CHIP DETECTOR AND METHOD OF USE

(71) Applicant: PRATT & WHITNEY CANADA CORP., Longueuil (CA)

(72) Inventor: Antwan Shenouda, Mississauga (CA)

(73) Assignee: PRATT & WHITNEY CANADA CORP., Longueuil (CA)

( * ) Notice: Subject to any disclaimer, the term of this patent is extended or adjusted under 35 U.S.C. 154(b) by 243 days.

(21) Appl. No.: 16/799,282

(22) Filed: Feb. 24, 2020

(65) Prior Publication Data

US 2021/0263009 A1    Aug. 26, 2021

(51) Int. Cl.
| | |
|---|---|
| *G01N 33/28* | (2006.01) |
| *F16N 29/04* | (2006.01) |
| *G01N 15/06* | (2006.01) |
| *G01V 3/10* | (2006.01) |
| *G01N 15/10* | (2006.01) |

(52) U.S. Cl.
CPC ......... *G01N 33/2858* (2013.01); *F16N 29/04* (2013.01); *G01N 15/0656* (2013.01); *G01V 3/101* (2013.01); *F16N 2210/08* (2013.01); *G01N 2015/1087* (2013.01)

(58) Field of Classification Search
CPC .. F16N 2210/02; F16N 29/04; F16N 2210/08; F16N 2200/04; G01N 15/0606; G01N 33/2858; G01N 15/0656; G01N 2015/0053; G01N 15/1031; G01N 2015/1087; G01N 33/28; G01N 15/06; G01V 3/10; G01V 3/101
See application file for complete search history.

(56) References Cited

U.S. PATENT DOCUMENTS

| | | | | |
|---|---|---|---|---|
| 4,100,491 | A * | 7/1978 | Newman, Jr. | G01V 3/08 340/606 |
| 5,264,832 | A * | 11/1993 | Parmer | G01N 15/0656 73/61.42 |
| 5,604,441 | A * | 2/1997 | Freese, V | G01N 33/2888 324/663 |
| 5,674,401 | A * | 10/1997 | Dickert | G01N 33/2888 210/695 |
| 6,204,656 | B1 * | 3/2001 | Cheiky-Zelina | G01R 27/2617 324/687 |
| 7,068,027 | B1 | 6/2006 | Mastro et al. | |
| 10,197,488 | B2 | 2/2019 | Youssef | |
| 10,317,354 | B2 | 6/2019 | Ricci et al. | |
| 2009/0314064 | A1 * | 12/2009 | Augros | F01M 11/10 73/61.42 |
| 2018/0364141 | A1 * | 12/2018 | Youssef | G01V 3/08 |

\* cited by examiner

*Primary Examiner* — Jermele M Hollington
*Assistant Examiner* — Suresh K Rajaputra
(74) *Attorney, Agent, or Firm* — Norton Rose Fulbright Canada LLP

(57) ABSTRACT

The magnetic chip detector system can have a first conductor member and a second conductor member both exposed to a liquid flow path and separated from one another by gap, each one of the conductor members having a magnetic field oriented into the liquid flow path, at least a first one of the magnetic fields being actively modifiable; an electrical energy source configured to induce a current circulation across the gap; and a meter configured to measure a response of the gap to the induced current circulation.

19 Claims, 13 Drawing Sheets

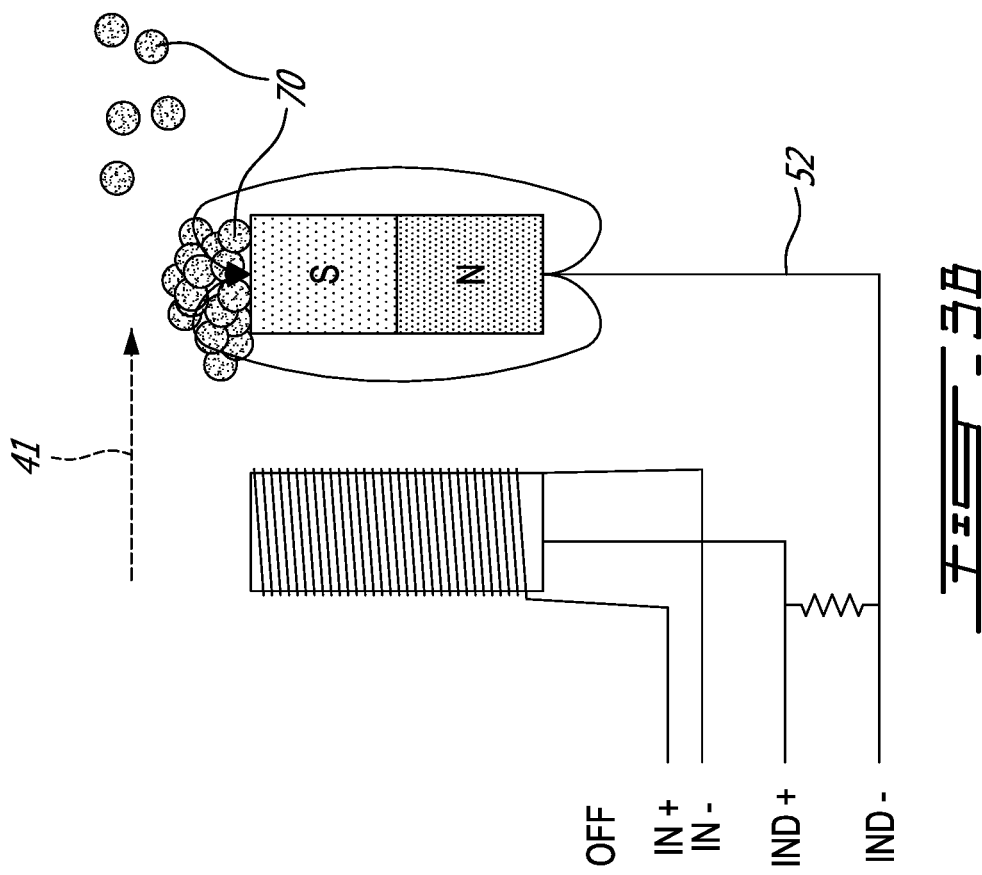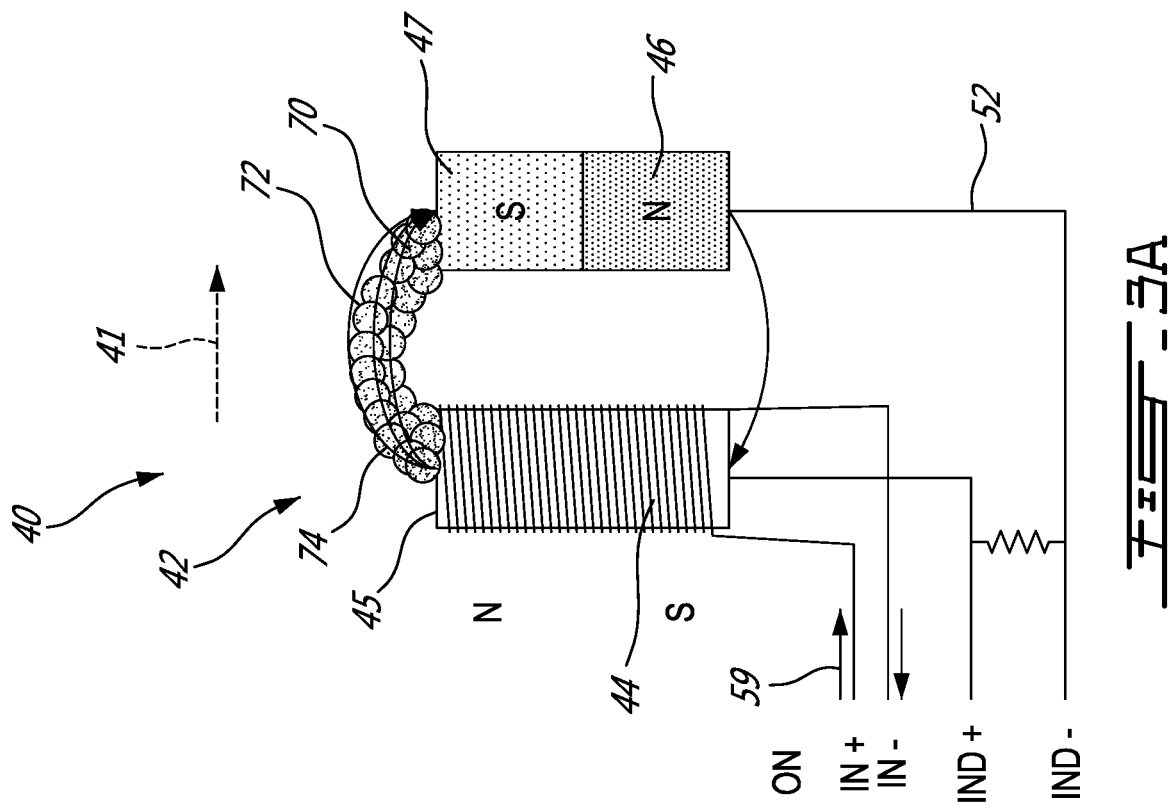

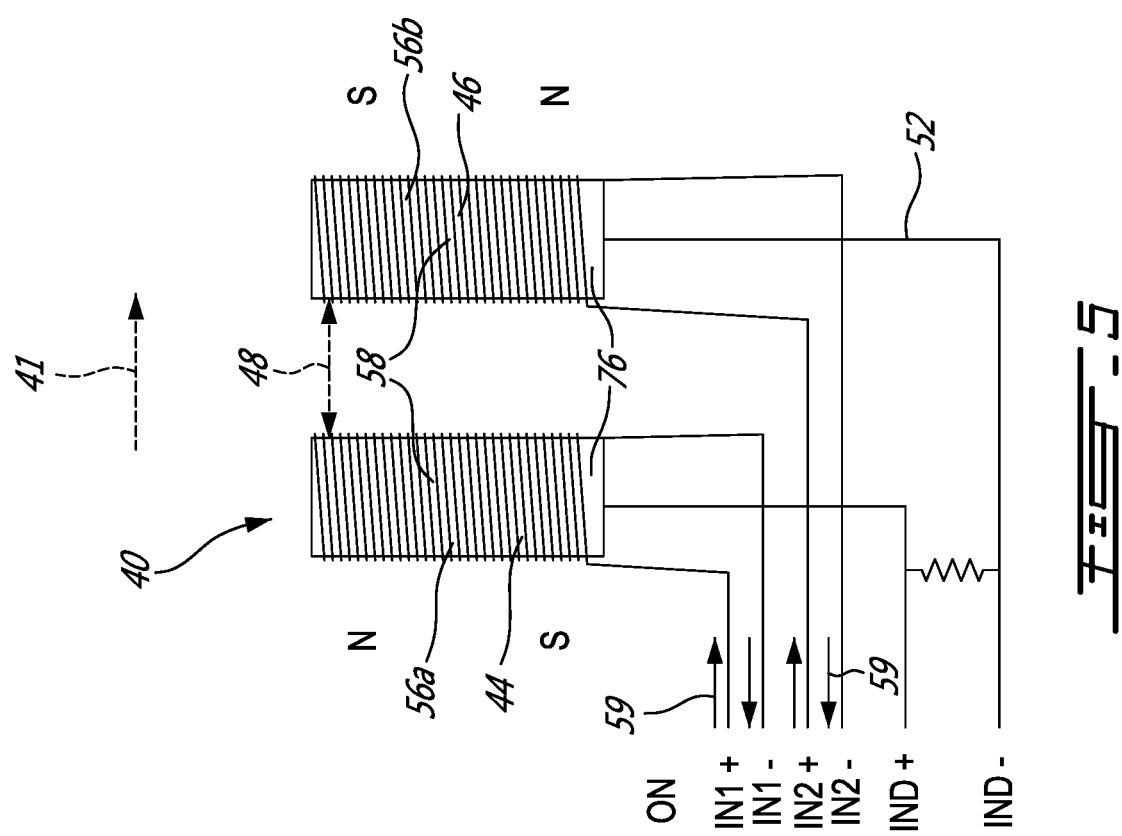

MAGNETIC CHIP DETECTOR AND METHOD OF USE

TECHNICAL FIELD

The application relates generally to gas turbine engines and, more particularly, to systems for detecting metallic particles in a liquid flow therein.

BACKGROUND OF THE ART

The presence of metallic particles in a liquid flow in an engine, such as the oil flow or coolant flow, for instance, can be an indication of component wear, malfunction, or impending failure, this can be the case for components such as engine gears or bearings for instance. To this end, metal particle detectors have been used to detect the presence of such metallic particles. While known metal particle detectors have been satisfactory to a certain degree, there always remains room for improvement. For instance, some known metal particle detectors were prone to false indications (such as false positive detection of metal particle), and as a result, engine checks and/or engine maintenance was performed more than necessary, representing an undesired source of cost, and a source of frustration, to the operator.

SUMMARY

In one aspect, there is provided a magnetic chip detector system comprising: a first conductor member and a second conductor member both exposed to a lubricant path and separated from one another by gap, each one of the conductor members having a magnetic field oriented into the lubricant path, at least a first one of the magnetic fields being actively modifiable; an electrical energy source configured to induce a current circulation across the gap; and a meter configured to measure a response of the gap to the induced current circulation.

In another aspect, there is provided a method of monitoring lubricant in an engine, the method comprising, in sequence: generating a magnetic field in a first orientation around at least a first conductor member, the first conductor member and a second conductor member separated from one another by a gap exposed to a flow of the lubricant, the conductor members forming part of an electrical circuit including the lubricant flow area across the gap; increasing a strength of a magnetic field in a second orientation, opposite the first orientation, around the second conductor member; inducing an electric current across the circuit, and measuring a response of the circuit to the induced electric current; providing an indication of presence or absence of ferromagnetic chips in the lubricant based on the measured response of the circuit.

DESCRIPTION OF THE DRAWINGS

Reference is now made to the accompanying figures in which:

FIGS. 3A-3C show a sequence of steps of another example method of use of the embodiment shown in FIGS. 2A and 2B, addressing the collection of small metallic particles

FIG. 5 shows a second embodiment of a magnetic chip detector;

DETAILED DESCRIPTION

Figure 1:
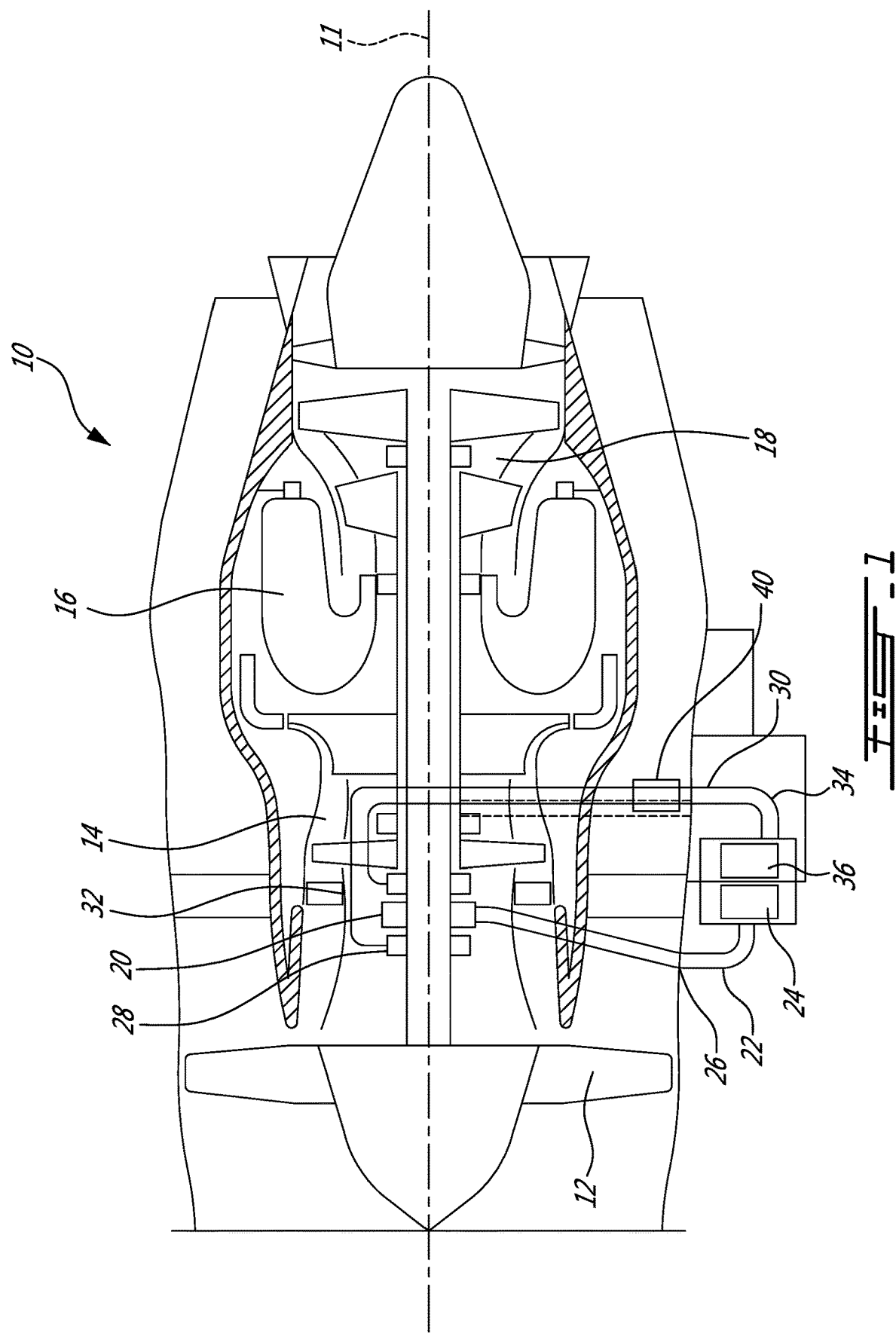
FIG. 1 is a schematic cross-sectional view of a gas turbine engine.

FIG. 1 illustrated a gas turbine engine 10 of a type preferably provided for use in subsonic flight, generally comprising in serial flow communication a fan 12 through which ambient air is propelled, a compressor section 14 for pressurizing the air, a combustor 16 in which the compressed air is mixed with fuel and ignited for generating an annular stream of hot combustion gases, and a turbine section 18 for extracting energy from the combustion gases.

The compressor 14, fan 12 and turbine 18 have rotating components which can be mounted on one or more shafts. Bearings 20 are used to provide smooth relative rotation between a shaft and casing (non-rotating component), and/or between two shafts which rotate at different speeds. An oil lubrication system 22 including an oil pump 24, sometimes referred to as a main pump, and a network of conduits and nozzles 26, is provided to feed the bearings 20 with oil. Seals 28 are used to contain the oil. A scavenge system 30 having cavities 32, conduits 34, and one or more scavenge pumps 36, is used to recover the oil, which can be in the form of an oil foam at that stage, from the bearings 20. Oil conduits are also use to and from gearing, and/or to and from auxiliary components, for instance. It is relatively typical to use one or more air-oil separator and one or more filter between the scavenge system 30 and the nozzles 26 to control the quality of the lubricant being supplied to the bearings.

The presence of metallic chips in the scavenge system 30 can be an early indication of component wear or even component failure. Accordingly, it can be desired to provide a chip detector 40 in the scavenge system 30. A single chip detector 40 may be used, which may be located immediately upstream of the scavenge pump 36 or filter(s) for instance, or multiple chip detectors can be used, e.g. in a main scavenge line, in a plurality of scavenge line segments forming part of a scavenge line network, etc.

To detect metallic chips of ferromagnetic materials such as iron, cobalt, nickel and some associated alloys (e.g. steel), a magnetic chip detector 40 can be used.

A first example of such a magnetic chip detector 40 is presented in FIG. 2. This magnetic chip detector 40 includes two conductor members 44, 46, which can be exposed to a flow 41 in the fluid path 42 (here a scavenge oil path), and separated from one another by a gap 48 of non-conductive material (e.g. electrical insulator) having a given width. The conductor members 44, 46 can be prongs or discs of electrically conductive material to name two possible examples. As will be seen in greater detail below, active or passive magnetic fields can be associated to the conductor members, and therefore, it will be understood that the conductor members can be permanent magnets, have permanent magnets included within a body, or simply be a non-magnetic material surrounded by a coil, to name some examples. The conductor members 44, 46 can be individually held with a tip 45, 47 exposed to the lubricant path 42, in sockets of non-conductive material, for instance, or collectively held in a body of electrically insulating material such as plastic, which itself serves as a plug configured to be received in a corresponding socket, to name another possible example. The conductor members 44, 46 can be permanently embedded into a non-conductive material, such as by being overmoulded by non-conductive material, which may be a non-conductive material of the scavenge oil line, to name yet another example. Numerous variants are possible and the details can be selected as a function of the specificities of a targeted implementation. The conductor members 44, 46 can be said to have axes oriented towards/into the fluid path 42. An electrical energy source 50 is provided and configured in a manner to allow inducing a current along a circuit path 52 extending from one of the conductor members 44 to the other 46 across the fluid path 42, and a meter is provided to measure a response of the circuit path 52 to the induced current. The purpose and use of these two latter components will be detailed below.

The magnetic chip detector 40 is further configured in a manner to allow magnetic fields to be emitted in general alignment with the axes of the conductor members 44, 46. At least one of the magnetic fields is active, in the sense that it can be controllably modified. In the example presented in FIGS. 2A and 2B, a second one of the magnetic fields is passive, and imparted here by means of using a second conductor 46 in the form of a permanent magnet 54, whereas the first magnetic field is active, and imparted here by means of using an electromagnet 56, and more specifically by circulating current along a coil 58 wrapped around a conductive core. In alternate embodiments, two active fields can be used for instance. There are different ways to achieve an active magnetic field, and in other embodiments, both the magnetic fields can be active. Several example variants will be presented below.

The magnetic chip detector 40 can have numerous potential control schemes. A relatively simple first one will now be described with reference to FIGS. 2A and 2B. In a first step, shown in FIG. 2A, a magnetic field is emitted in coincidence with the second conductor member 46, which is achieved here via the permanent magnet 54 material of the conductor member 46. A first pole 62 of a chip 60 of ferromagnetic material is pulled into continued contact with the second conductor member 46 via the magnetic force exerted by the interaction between the magnetic field and the ferromagnetic material. This force can be stronger than any contrary force which may be exerted onto the chip 60, such as a force resulting from the viscosity of the fluid 66 circulating in the fluid path 42 against the chip 40, and which may tend to pull the chip 40 away from the second conductor member 46.

In the first step, the magnetic field around the first conductor member 44 can be nil, or otherwise insufficient to pull the opposite pole 62 of the chip 40 against it (e.g. the field may be of the opposite polarity/orientation but of lesser amplitude than the field emitted around the second conductor member 46, or of the same polarity/orientation, for instance). In the electrical circuit path 52 from the tip 45 of the first conductor member 44 to the second conductor member 46, there is a significant electrical barrier formed by the presence of the fluid 66, which has an electrical conductivity significantly lower than the electrical conductivity of the conductor members 44, 46 and of the chip 60. The electrical circuit path 52 extending from the first conductor 44 to the second conductor 46 across the fluid circulation area is thus open.

Electrical conductors typically have a resistivity value orders of magnitude less than $1\Omega \cdot m$ (e.g. iron, a good conductor, has a resistivity of $9.7\times10^{-8}\Omega \cdot m$, and ferromagnetic materials are typically good conductors), whereas electrical insulators typically have a resistivity value orders of magnitude more than $1\Omega \cdot m$ (e.g. hard rubber, a good insulator, has a resistivity in the order of $10^{13}\Omega \cdot m$), and it is therefore quite straightforward for a person having ordinary skill in the art to discern one from the other. Engine oil is typically a good electrical insulator, and can have conductivity values of less than 10 pS/m, for instance, and a wall of oil can thus be very efficient in opening an electrical circuit.

In a second step, while the magnetic field around the second conductor member 46 is maintained, maintaining the electrical contact with the corresponding pole 62 of the chip 60, the amplitude of the magnetic field around the first conductor member 44 is increased in the orientation opposite to the magnetic field around the second conductor member 46 until reaching at least a level of amplitude at which the magnetic force between the first conductor member 44 and the corresponding, opposite pole 64 of the chip 60 overcomes any other existing force and brings the opposite side of the chip 60 into electrical contact with the first conductor member 44. Here, the chip 60 acts as a switch and closes the electrical circuit 52 between the two conductor members 44, 46, across the fluid path 42. This can be achieved in this example by applying electrical energy to circulate electrical current 59 along the coil 58 to activate the electromagnet 56. If electrical current 59 was already circulated along the coil 58, its magnitude can be increased in a scenario where it was of anti-parallel orientation, or its orientation can be reversed in a scenario where it was previously of parallel orientation, to name two examples, all of which will generally be considered as increasing the strength of the magnetic field in an orientation opposite to the orientation of the field across the second conductor member 46 for the purpose of this specification.

The presence of the chip 60 can be detected at this stage by obtaining an indication of the response of the circuit path 52 extending from one conductor member 44 to the other 46 across the fluid path 42 to an induced current circulation, such as via the measurement of the resistivity of the circuit path for instance. Indeed, the resistivity will be significantly lower if a chip 60 is closing the circuit 52, than if a wall of fluid 66 is opening the circuit 52. Various means can be used to obtain an indication of the resistivity of that circuit 52 segment. For instance, a difference of potential can be applied across the conductors 44, 46, and the resulting amplitude of electrical current can be measured and compared to a reference value. The reference value can be a predetermined threshold value, for instance, or a value associated to a certain, relatively sudden, change from an earlier-measured value (associated to an absence of a chip 60), to name two examples. Due to the relationship of V=RI, various alternative ways of measuring the response of the circuit 52 are possible, and these alternative ways will typically involve inducing an electric current across the circuit 52 segment in one form or another. The comparison can be based on electronic hardware, logic gates, and/or involve functionalities provided by a computer, to name some examples, and can use techniques formerly known in the art. Once the response of the circuit 52 segment to the induced current has been associated to a presence of a chip 60, a suitable indication can be triggered. If the magnetic chip detector 40 is used in an engine of an aircraft 10, for instance, a visual indicator or an audible alarm can be displayed in the cockpit. The visual indicator can be in the form of an icon on a display screen, or of a light which becomes turned on, for instance. The association between the response of the circuit 52 segment and the absence of a chip 60 can be positively indicated, or alternately, an indicator of chip 60 presence can simply be de-activated unless a chip 60 is positively identified. In this specific embodiment, a bridge resistance 68 is used between electrical contacts leading to the two conductor members 44, 46, but such a configuration is optional.

As represented in FIG. 3, in a context where magnetic fields of opposite orientations are sustained around the first conductor member 44 and the second conductor member 46, respectively, for a long period of time, small ferromagnetic particles 70 carried in the fluid flow 41 may be pulled into contact with both conductor members 44, 46, and pile onto one another until they eventually amalgamate, aligning along the magnetic field lines 72, into a bridge 74 which closes the electrical circuit 52 segment between the exposed tips 45, 47 of the conductor members 44, 46. Such small ferromagnetic particles 70 may result from normal wear, and not be a cause of alarm. Obtaining an indication of resistivity along that circuit 52 segment, at that time, may lead to falsely concluding to the alarming presence of the a chip 60, and therefore direct the aircraft to engine 10 check/premature maintenance, whereas the alarm simply resulted from normal wear and the engine 10 was not yet to be performed maintenance upon. This can be a cause of undesired maintenance costs. Such a situation can be avoided by performing a method such as described above in relation with FIGS. 2A and 2B, which can involve preceding the period of monitoring circuit 52 segment response with a period where the actively controlled magnetic field(s) are controlled in a manner to avoid the formation of such a bridge 74.

Figure 2B:
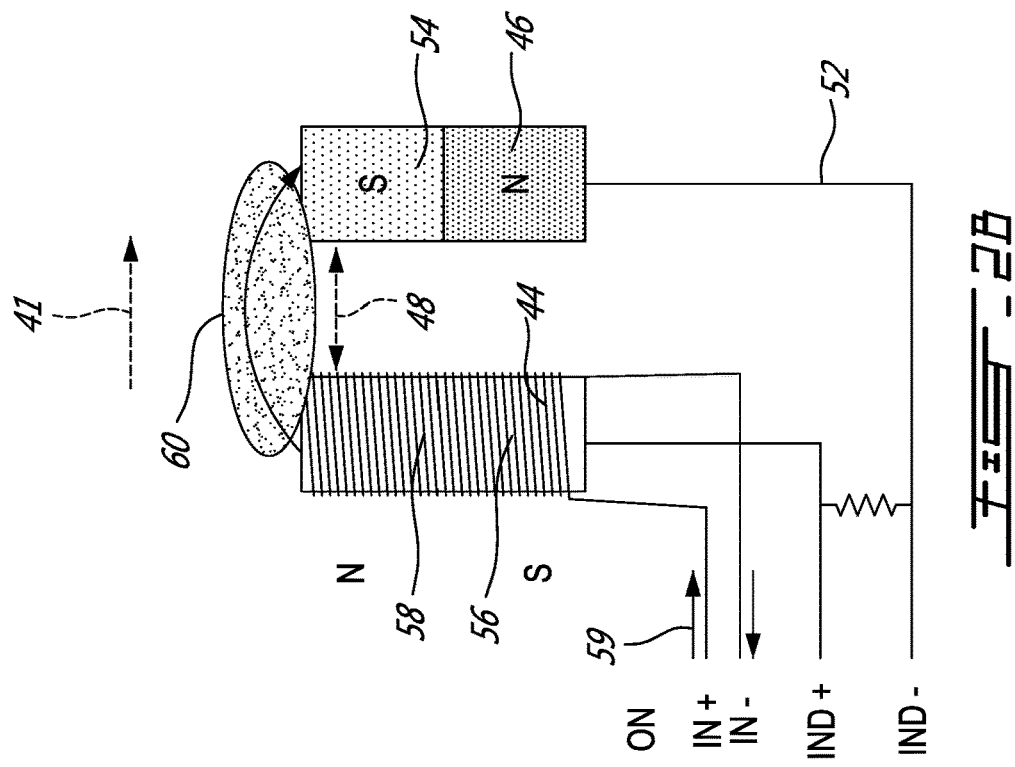
FIG. 2A and FIG. 2B are a first embodiment of a magnetic chip detector showing a sequence of two steps in accordance with one possible method of use.

Accordingly, in one embodiment, it can be desired to intermittently operate the chip detector 40 in a chip attraction mode, during which it can magnetically attract a chip 60 while avoiding smaller particles 70 (e.g. in the configuration of FIG. 2A), and in a chip diagnostic mode, during which it can forcefully bridge the gap with any attracted chip 60, and detect the presence of the chip 60 via the exhibited electrical resistance (e.g. configuration of FIG. 2B). Henceforth, one mode of operation can include regularly alternating between these two modes of operation. Moreover, given principles of electromagnetism which will be detailed below, to break a bridge formed of smaller particles such as fuzz, one may wish to vary one or both of the two magnetic fields.

It will be noted that once a chip has been caught into contact with the two conductor members in a manner that it bridges the electrical circuit between the two conductor members, reducing the strength of one of the fields in a manner sufficient to break a bridge which would have consisted of fuzz, may not cause a larger chip to open the circuit, given the retention force offered by the other conductor member. Accordingly, simply continuing to detect the presence of an electrical current across the gap while the electromagnetic fields are being in a manner which is incompatible with the formation of a fuzz bridge across the gap may provide a suitable indication that a chip, and not fuzz, is present in the liquid flow path.

The chip detector 40 can even be designed in a manner to specifically detect only chips 60 above a certain size. One possible way to achieve this is to select a gap 48 width between the conductor members 44, 46 as a function of the desired minimum chip 60 size. The gap width can be of between 0.020" and 0.060" in some embodiments, for instance, more specifically of between 0.030 and 0.050" in some embodiments, and can be specifically of roughly 0.040" in some embodiments.

Figure 2A:
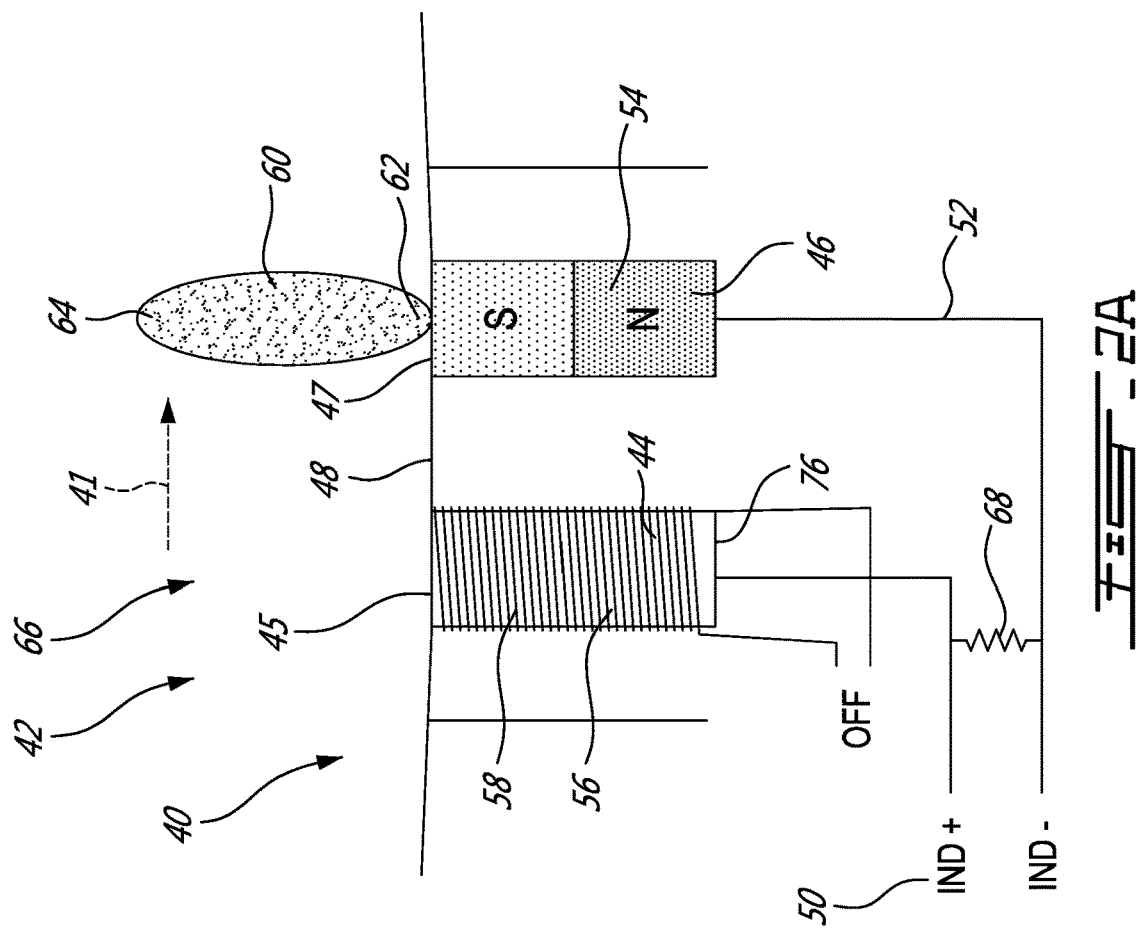

In another mode of operation, the chip detector 40 can be used first in a first configuration (e.g. such as FIG. 2B) where it may attract either chips 60 or particles 70 (aka fuzz), and upon detecting a possible chip 60 presence via the resistivity of the circuit 52 segment, the chip detector 40 can be switched to a mode such as shown in FIG. 2A, to flush smaller particles 70 or fuzz with the lubricant flow 41 while continuing the attraction of any chip 60 to the conductor members 44, 46, and then switched back to a configuration such as FIG. 2B, to either confirm or cancel the earlier determination of chip detection. Several other modes of operation are possible, some of which will be described below, but some relevant theory will first be discussed.

Principle 1:

The force between a magnet and a ferromagnetic object is inversely proportional to the distance between them. This means that a strong magnetic field is initially required to attract distant chips 60 flowing in oil 66, but once the chips 60 are attracted to the prong, the magnetic force required to keep them attached is much less since the distance between the chip 60 and the prong is effectively zero. Therefore, a large chip 60 can still be attached to either or both prongs when one field is turned off or reversed, because the field of the other prong holds the chip 60 firmly. The force between two magnets is given by the following equation.

$$F = \frac{\mu q_{m1} q_{m2}}{4\pi r^2}$$

where

F is force (SI unit: newton)

$q_{m1}$ and $q_{m2}$ are the magnitudes of magnetic poles (SI unit: ampere-meter)

μ is the permeability of the intervening medium (SI unit: tesla meter per ampere, henry per meter or newton per ampere squared)

r is the separation (SI unit: meter).

Principle 2:

When the fields of both prongs point to the same direction, they repel each other. As a result, any small chips/fuzz 70 adjacent to each other that are bridging 74 the gap 48 between the prongs, will separate, resulting in an open circuit. However, large chips 60 bridging the gap 48 may continue to be retained.

Principle 3:

A single large ferromagnetic chip 60 bridging the gap 48 between two prongs is more strongly attracted than multiple smaller chips 70 (fuzz) magnetically attracted together in the presence of the magnetic field between the prongs. This is because multiple ferromagnetic chips 70 introduce multiple boundaries or air (oil) gaps between themselves and between them and the prongs, thus weakening the magnetic flux through them, while a single chip 60 only has two air (oil) gaps. In FIG. 3, darker color is used to represent particles 70 which are more strongly attracted.

The embodiment shown in FIG. 2A can be considered a four pin, single coil, electromagnet 56 & permanent magnet 54 conductor member design. In this specific embodiment, the conductor members 44, 46 are prongs. A single coil 58 is wrapped around a ferromagnetic core 76 to form an electromagnetic prong. When the electromagnet 56 is activated, it generates a field opposite that of the permanent magnet 54 prong. A voltage or current can be applied to IND+ & IND− and the impedance between these points can be measured. As ferromagnetic debris is collected between the prongs 44, 46, the measured impedance will change resulting in a chip 60 indication. The optional resistor 68 can be used to detect dormant failures. When the engine is shutoff, any collected debris will remain attracted to the prongs 44, 46 because the field of the permanent magnet 54 is still active. The electromagnet 56 has a control coil 58 wound around it to control its magnetic field strength and direction by varying the applied current 59. Table 1 below represents different potential states:

TABLE 1 example potential states of a two conductor member design where one conductor member has an active magnetic field and the other one has a passive magnetic field

| State | Prong 1 Current | Prong 1 Field | Prong 2 Field | Effect |
| --- | --- | --- | --- | --- |
| Chip Detector (Opposite field) | Positive | N-S | S-N | Attract chips between prongs |
| OFF | Off | Nil or residual N-S | S-N | Attracted chips weakly attached to probe 1, Small chips are shed from probe 1. Chips firmly attached to probe 2. |
| Opposing (Similar field) | Negative | S-N | S-N | Small chips bridging the gap repel each other and break the gap. Large chips still bridge the gap. |

Figure 3C:
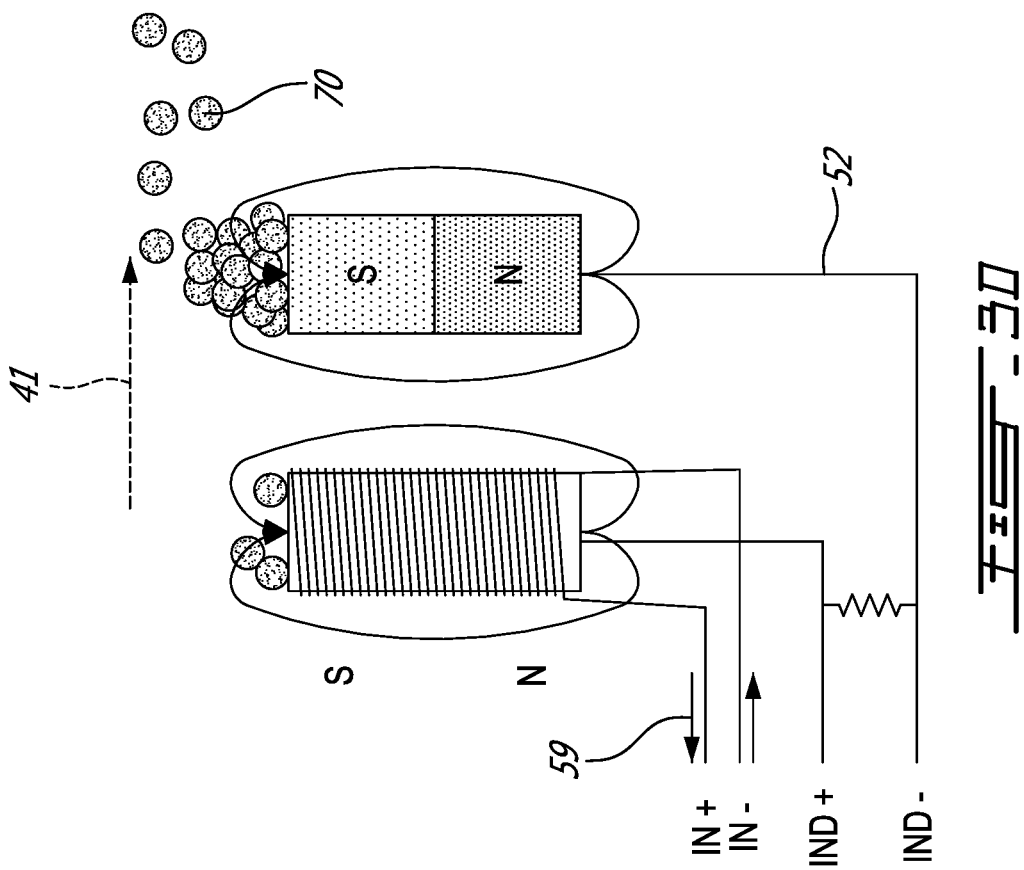
Figure 3D:
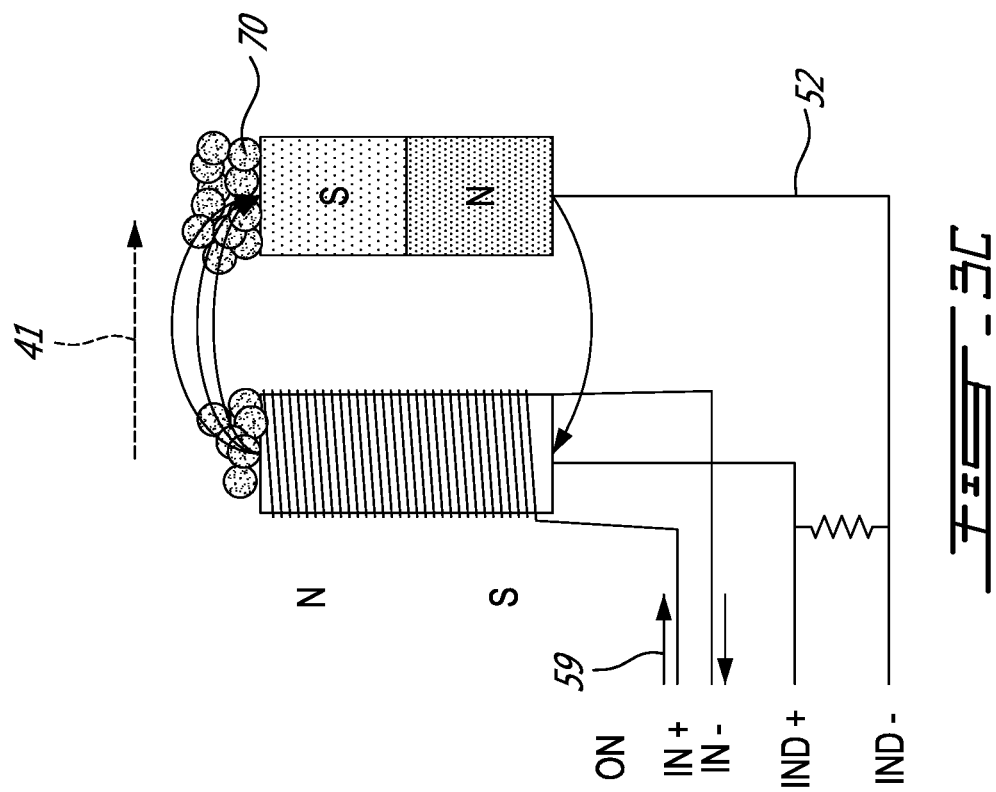
FIG. 3D is a variant of FIG. 3B.
Figure 4A:
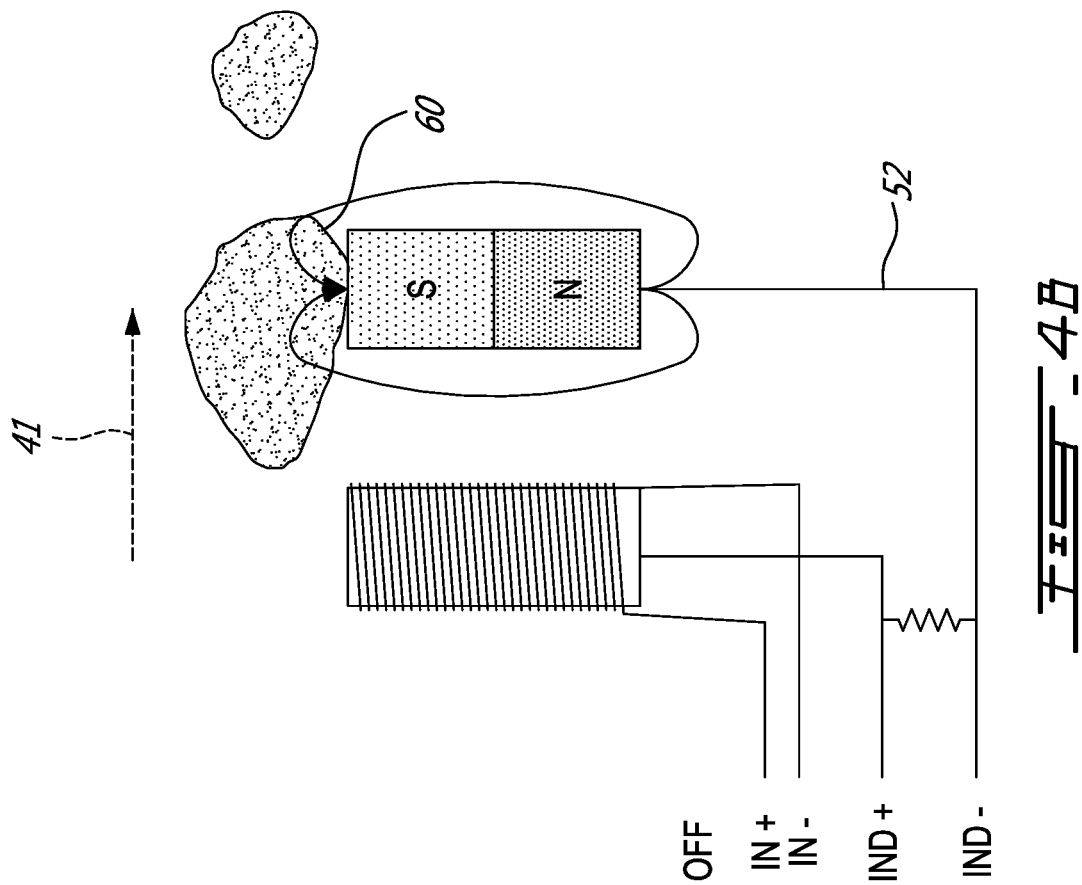
FIGS. 4A-4C show a sequence of steps of another example method of use of the embodiment shown in FIGS. 2A and 2B, addressing the collection of a metallic chip above a given size.
Figure 4B:
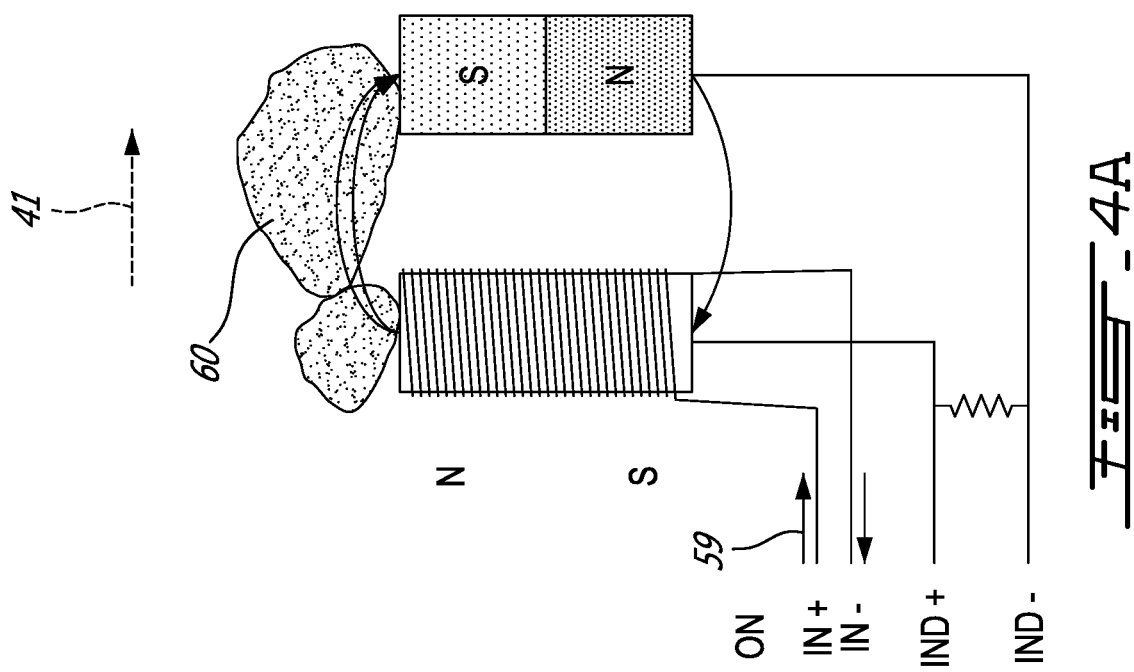
Figure 4D:
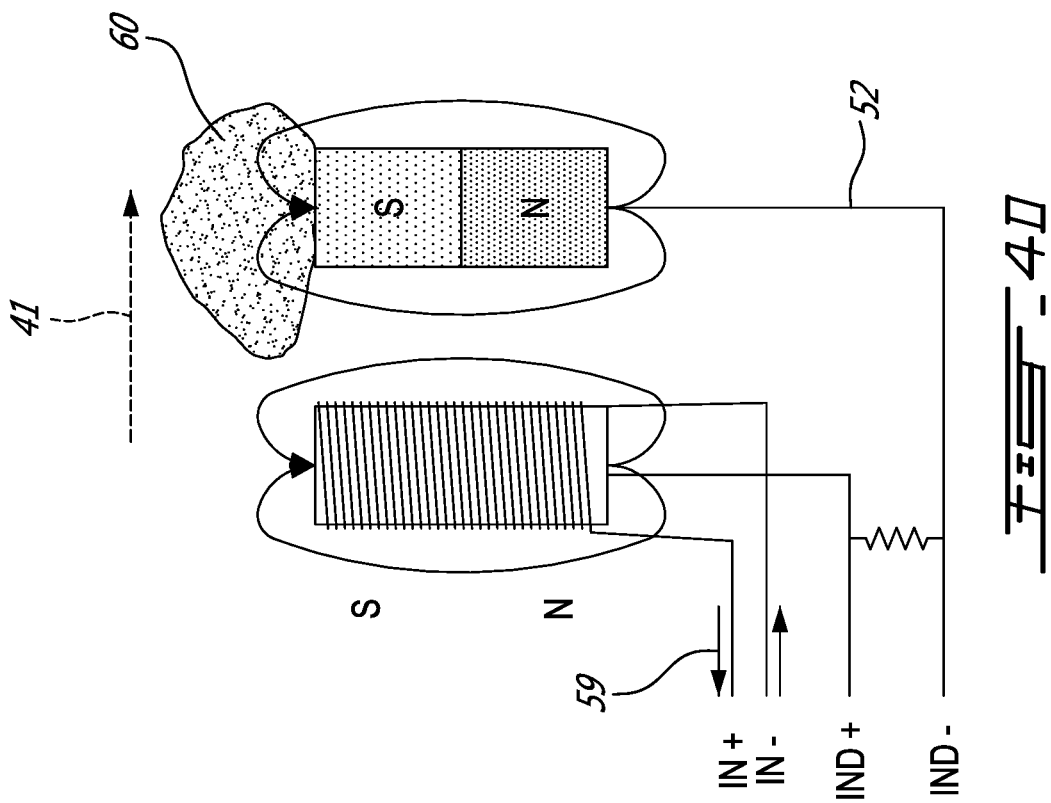
FIG. 4D is a variant of FIG. 4B.
Figure 4C:
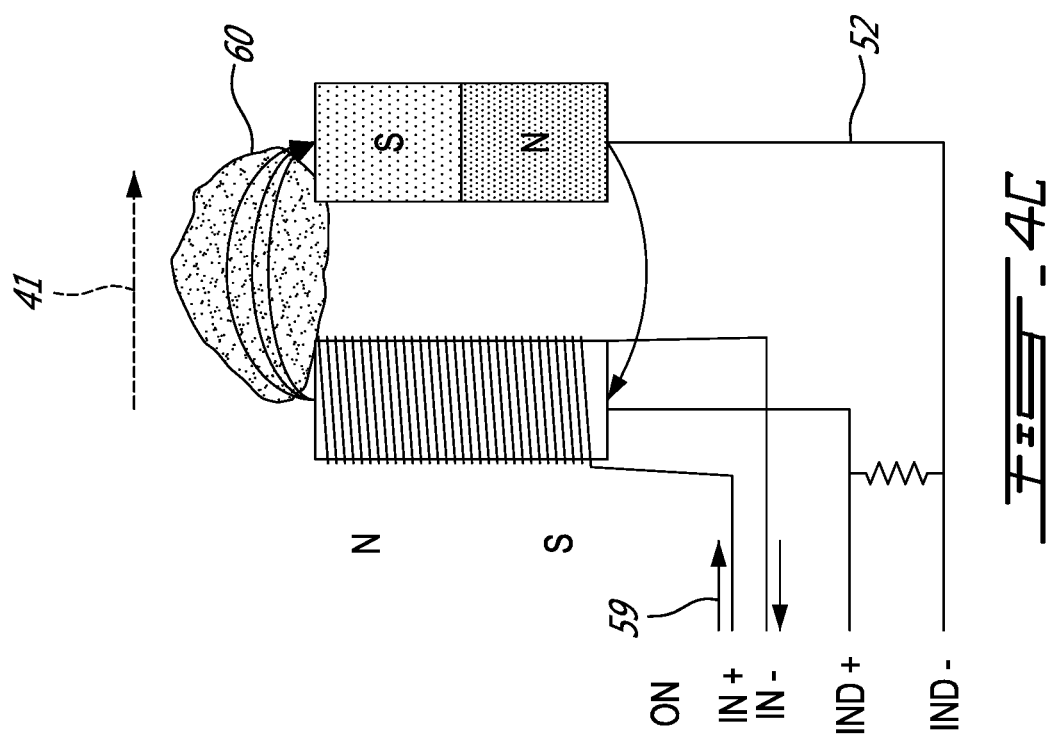

As presented above, methods of operation may use only the two first states presented in Table 1. For instance, the detector can begin by being used in the OFF state, and the detector can check whether a chip 60 is present by switching to the chip detector state, which can be done once, intermittently, sporadically, or at a predetermined moment in time, for instance. Another method of operation using the two first states can operate in the chip detector state, and upon detecting the presence of ferromagnetic debris, switch to the OFF state, and then back to the chip detector state to obtain a first degree indication that the detection is actually a chip 60, and not just particles/fuzz 70. Such a sequence of operation is illustrated in FIGS. 3A to 4C, with FIGS. 3A to 3C showing the detection of particles/fuzz 70, and FIGS. 4A to 4C showing the confirmation of the detection of a chip 60.

Another possible mode of operation which can use the same hardware would be to go further and instead of just using the first two states, it can move to the third state (opposing fields) of Table 1 before returning to the second state (OFF) and then the first state. This is illustrated in FIGS. 3D and 4D. The third state may more efficiently rid the prongs 44, 46 of fuzz/small particles 70 (i.e. require less external drag force from the fluid 66) than the second state, because in the third state, any small particle 70 bridging the gap 48 will become polarized in a manner to repel each other. It will be noted that the application of current from one prong 44 to the other 46 in order to detect the reaction of the area between the prongs 44, 46 can be performed sporadically, in predetermined situations (e.g. in specific states), or permanently (e.g. throughout the different states), to name some examples. The exact choice of method is left to the designer in view of specific contexts.

More states are possible if two active conductor members are used. FIG. 5 shows one such possible embodiment where both conductor members 44, 46 are prongs in the form of electromagnets 56a, 56b, each one having a control coil 58 wound around a ferromagnetic core 76 to control its magnetic field strength and direction by varying the applied current 59. Each electromagnet 56a, 56b is electrically connected to a detection circuit 52 that can be activated, for instance, when a chip 60 bridges the gap 48 between them.

Each electromagnet 56a, 56b can be activated independently and can, for instance, be used in accordance with a method of operation such as one presented above. One notable difference is that if the power to electromagnets 56a, 56b is shut down at engine shut down, the magnetic field will significantly diminish, and can leave a weak residual magnetic field which may or may not be negligible. Some of the collected debris may be lost, while some other may remain. If hard magnetic material is used for the prong core 76, then the residual field will be strong. If soft magnetic material is used, then the residual field will be weak.

It will be noted that an embodiment having two active conductor members 44, 46 can further allow additional states, such as prong two off or prong 2 N-S. Accordingly, a possible more elaborated method of operation can be as presented in table 2.

TABLE 2 example method of operation with two active magnetic field conductor members

| Step | Prong 1 | Prong 2 | Effect |
| --- | --- | --- | --- |
| 0 | N-S | S-N | Chip Detector Active. Small and large chips are attracted to bridge the gap |
| 1 | OFF | S-N | Small chips shed from P1. Large chips bridging gap still attached to P2 |
| 2 | S-N | S-N | Any small chips bridging gap repel each other |
| 3 | S-N | OFF | Small chips shed from P2. Large chips bridging gap still attached to P1 |
| 4 | S-N | N-S | Chip Detector Active. Small and large chips are attracted to bridge the gap |
| 5 | OFF | N-S | Small chips shed from P1. Large chips bridging gap still attached to P2 |
| 6 | N-S | N-S | Any small chips bridging gap repel each other |
| 7 | N-S | OFF | Small chips shed from P2. Large chips bridging gap still attached to P1 |
| 8 | N-S | S-N | Chip Detector Active. Small and large chips are attracted to bridge the gap |

By turning off (or weakening the field) and reversing the polarity of one prong at a time, any small chips 70 that are not directly adjacent to the prongs (small chips adjacent to other smaller chips to form a bridge 74) can separate, breaking the bridge 74 between the prongs. Small chips 70 may also be released in the oil flow 41. However, large chips 60 that are adjacent to either prong will remain attached to the prong with the active field.

Figure 6:
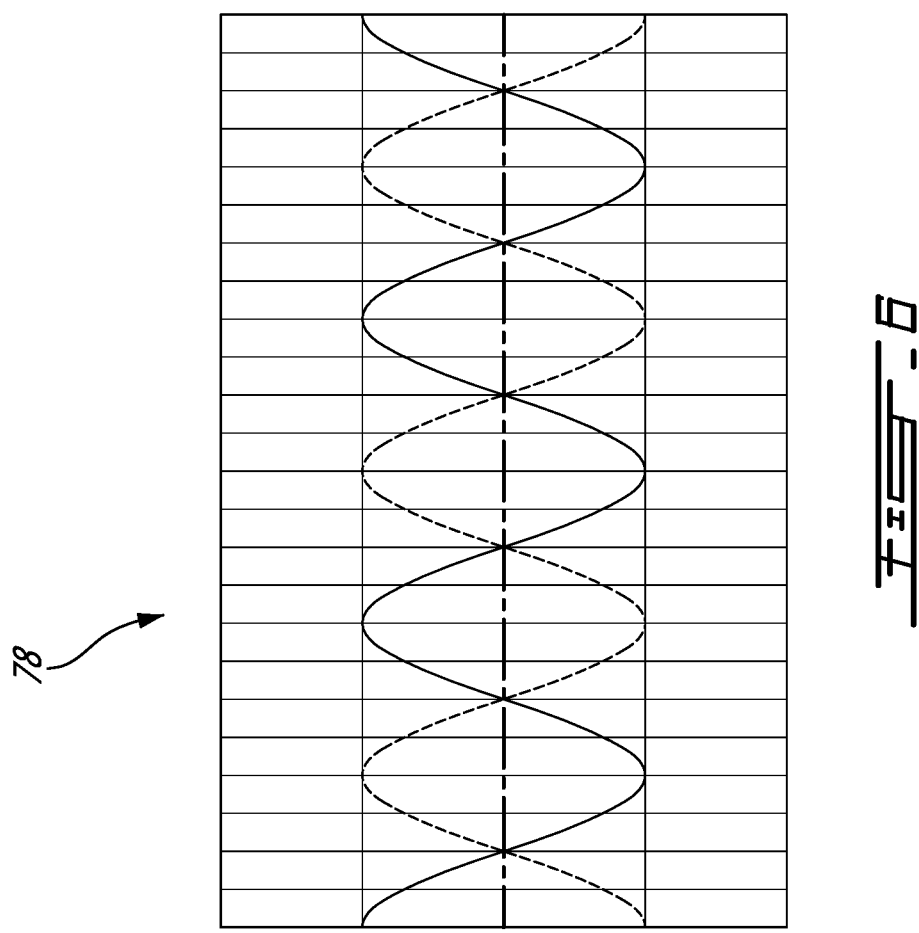
FIG. 6 shows current amplitude variation in alternating current, in accordance with one possible method of driving the coils in the embodiment of FIG. 5.

One possible method of operation embodying the method of Table 2 is to apply coil control current 59 in the form of discrete, square waves. Another one is to apply alternating current 78, such as presented in FIG. 6 for instance. The application of alternating current 78 can alternate the field directions and strengths between the prongs. A designer, with a view of a specific context, may wish to adapt frequency, waveform, and/or phasing angle with a view of attracting a certain size or type of chip 60 while rejecting others on a continuous basis.

Figure 7:
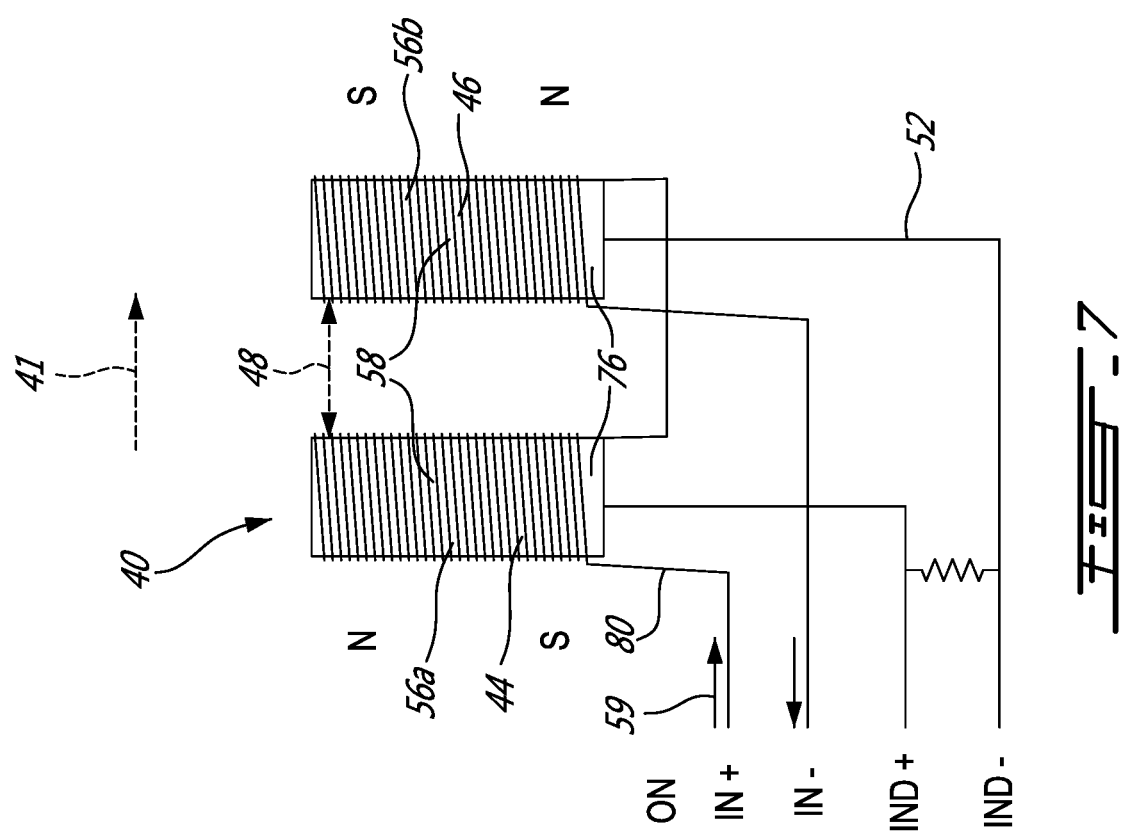
FIG. 7 shows another embodiment of a magnetic chip.

A variant of the embodiment shown in FIG. 5 is presented in FIG. 7, where the coils 58 of both prongs are on the same electrical circuit 80, but in an opposite orientation, allowing example states presented in Table 3.

TABLE 3 example states achievable with coils of two active
magnetic field conductor members on same circuit

| State | Probe Current | Probe 1 Field | Probe 2 Field | Effect |
|---|---|---|---|---|
| Chip Detector (Opposite field) | Positive | N-S | S-N | Attract chips between prongs |
| OFF | Off | Nil or residual N-S | Nil or residual S-N | Attracted chips weakly attached or fall off |
| Reverse | Negative | S-N | N-S | Small chips bridging the gap repel each other and break the gap |

Such an actively controlled chip detector 40 can have two electromagnets 56a, 56b; both electromagnets 56a, 56b sharing a control coil 58 wound around each one sequentially but in opposite direction to control their magnetic field strength and direction by varying the applied current 59. Each electromagnet 56a, 56b can be electrically connected to a detection circuit 52 that is activated when a measurement is taken. This chip detector 40 can be considered a 4 pin design. The coil 58 is wound in opposite directions such that applied current 59 to IN+ & IN− produces a North-South field in one prong and a South-North field in the other prong. The number of turns, or the diameter of the coil 58, may be different between each prong, thus producing unequal field strengths, or the same. As ferromagnetic debris is collected between the prongs, the measured impedance will change resulting in a chip 60 indication. The power to the electromagnets 56a, 56b can be turned off for prolonged periods, during which some of the collected debris may be lost, while some other may remain due to the weak residual magnetic field. For this design, when current 59 is turned off, the magnetic fields of both prongs can be eliminated simultaneously (or small residual field is present) since they share the same coil 58, in which case it may be difficult to reverse the field without losing large chips 60. In such a scenario, it can be preferred to reduce the field and strengthen it again.

Figure 8:
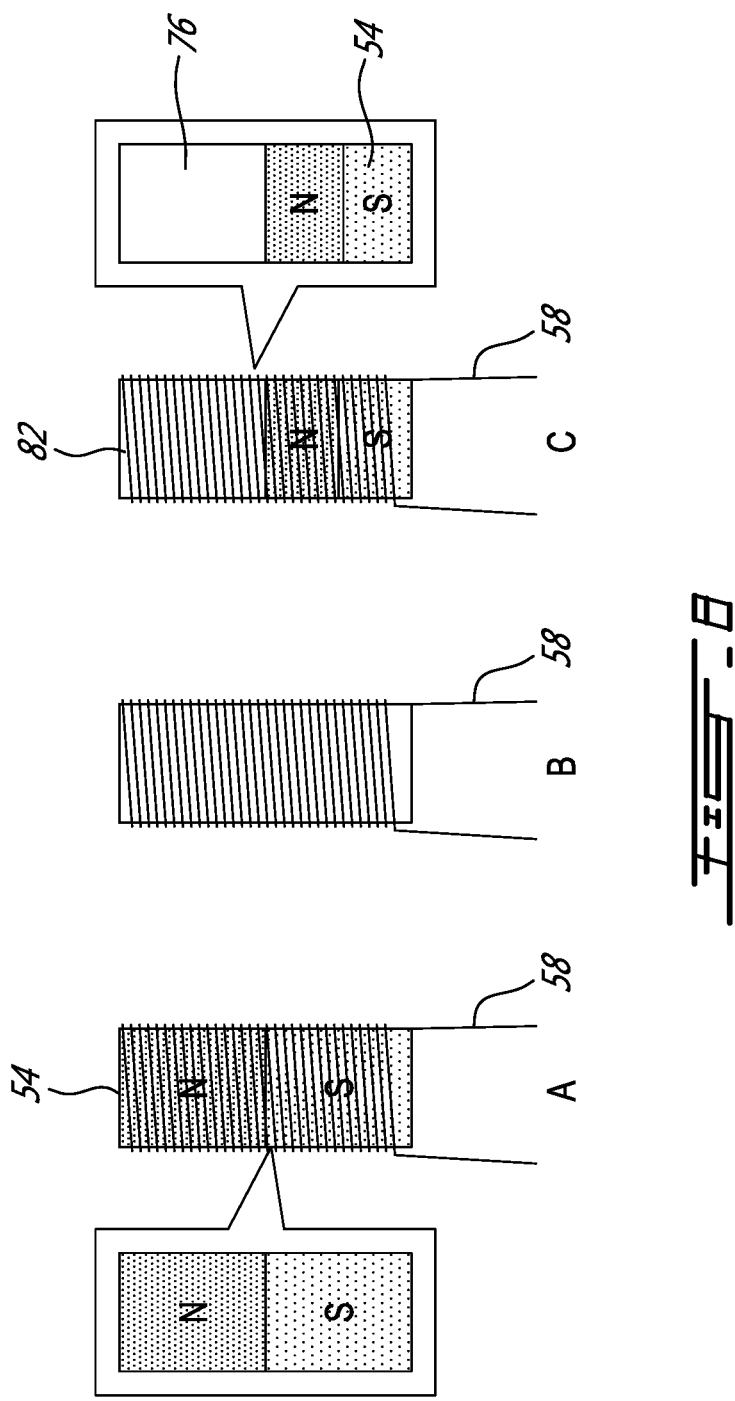
FIGS. 8A-8C show alternate embodiments of electromagnet designs which can be used as an active magnetic field conductor member in embodiments of a magnetic chip detector.

FIG. 8B presents an active electromagnet design such as presented above, whereas FIGS. 8A and 8C present two example alternate, hybrid electro-permanent magnet designs. The prong of FIG. 8B can only attract ferromagnetic chips 60 when current is applied to the coil 58. If the current is applied in one direction, it will produce a North-South electromagnet, if it is applied in the opposite direction it will produce a South-North electromagnet. The operation can switch between a given amplitude, negative and/or positive, and zero, or be tuned progressively such as to reduce and then re-augment the amplitude. At zero current, a residual field may be present. Depending on the details, collected chips 60 may still remain attached when current is turned off due to the residual field.

The embodiment shown in FIG. 8A is an electromagnet with a magnetic offset—created by winding a coil 58 on a magnet 54. FIG. 8C is an electromagnet including a coil 58 wrapping a core 82 made two components in series: a ferromagnetic core 76 and a permanent magnet 54. In alternate embodiments, the coil 58 can be wrapped around the ferromagnetic core 76, the permanent magnet 54, or both. All these active prongs can have the ability to control the collection of chips 60.

An interesting feature of using a hybrid design is that the coil 58 can be used to potentially cancel out, or lower, the magnetic field of the permanent magnet 54. Accordingly, a chip detector 40 using a hybrid design as an electromagnet can be used in accordance with one or the other of the methods presented above, by activating the coil 58 to reduce, cancel, or even potentially reverse the permanent magnet 54 magnetic field rather than activating a coil 58 to generate a field around a non-magnetic core. The former fails to a permanent magnetic field, whereas the latter fails to a potentially nil or weak magnetic field. Accordingly, the former may be preferred to allow the chip detector 40 to maintain its functionality in the event of a failure of the coil 58 or of the coil's power system.

Figure 9:
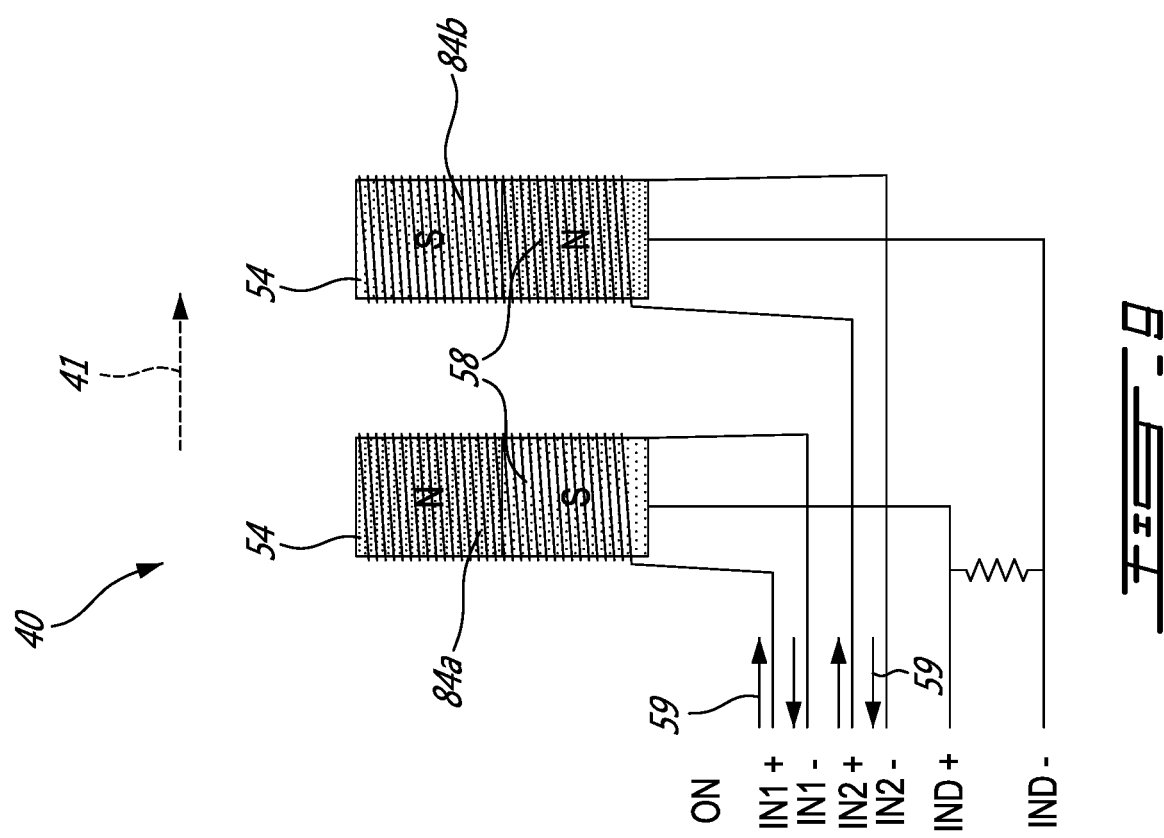
FIG. 9 shows another embodiment of a magnetic chip detector using active magnetic field conductor members in accordance with the embodiment of FIG. 8A.

An example chip detector 40 using two magnetic conductors members based on a hybrid design based on FIG. 8A is presented in FIG. 9. Example states achievable with such a chip detector are presented in Table 4, below:

TABLE 4 example states achievable with two hybrid active/passive
magnetic field conductor members

| Function | Probe 1 Current | Probe 1 Field | Probe 2 current | Probe 2 Field | Effect |
|---|---|---|---|---|---|
| Chip Detector (Opposite field) | Off | N-S | Off | S-N | Attract chips between prongs |
| OFF | Positive (−Hci) | Nil or residual N-S | Positive (−Hci) | Nil or residual S-N | Attracted chips weakly attached or fall off |
| One Probe Off | Positive (−Hci) | Nil or residual N-S | Off | S-N | Small chips on deactivated probe fall off. |
| Opposing (Similar field) | Positive+ | N-S (may demagnetize) | Off | S-N | Small chips bridging the gap repel each other and break the gap |

TABLE 4-continued example states achievable with two hybrid active/passive
magnetic field conductor members

| Function | Probe 1 Current | Probe 1 Field | Probe 2 current | Probe 2 Field | Effect |
|---|---|---|---|---|---|
| Reverse | Positive+ | S-N (may demagnetize) | Positive+ | N-S (may demagnetize) | Fields are reversed but oppose each other |

Figure 10:
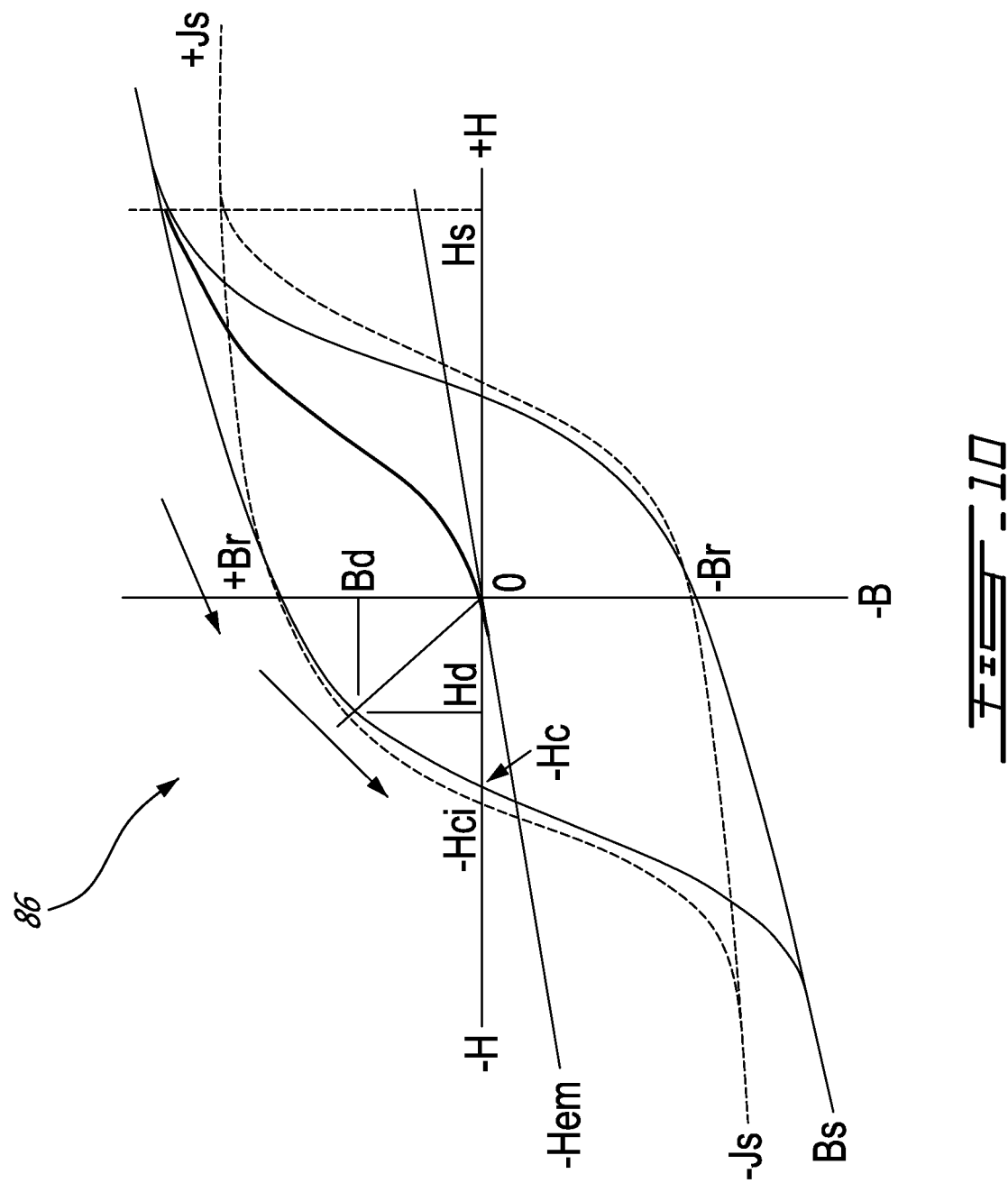
FIG. 10 shows an example hysteresis loop for a method of using an active magnetic field conductor member having an intrinsic permanent magnetic field.

Hybrid electro-permanent magnetic prongs can attract ferromagnetic chips 60 even when there is no current 59 applied to the coil 58. The magnetic attraction can be increased if power is applied and produces a field in the same direction as the permanent magnet and if the electro-magnet is not yet saturated. The magnetic field can be reduced, eliminated or reversed if the field produced by the current 59 is acting opposite to the permanent magnet 54 field. It's important to note that in order to prevent demagnetization of the permanent magnet 54, the applied H field should not exceed −Hci when applied in the reverse direction. In other words, the applied current 59 should not cause the H field to drop below −Hci. FIG. 10 represents an example hysteresis loop 86, or magnetization and demagnetization curve, and reference can be made to this curve 86 to illustrate this principle (see arrows). Indeed, a permanent electromagnetic field can be applied, or removed, from a ferromagnetic material by the application of an magnetic field.

Referring back to FIG. 9, such a design can be considered a six pin, two coil, independent electro-permanent magnetic prong design. The actively controlled chip detector 40 can have two permanent-magnets 54; each one having a control coil 58 wound around it to increase, reduce, eliminate or reverse its magnetic field by varying the applied current 59. Each coil 58 is wrapped around a permanent magnet 54 prong to form two electrically controlled permanent magnet prongs. Each electro permanent magnet 84a, 84b is activated independently. Like traditional chip detectors, one permanent magnet prong is oriented in a North-South orientation, while the other is oriented in a South-North orientation. However, an independent coil 58 is wrapped around each permanent magnet 54 in such a way that when the coil 58 currents 59 are activated, they weaken the magnetic field of the associated permanent magnet 54. As ferromagnetic debris is collected between the prongs, the measured impedance will change resulting in a chip indication. When the engine is shutoff, any collected debris will remain attracted to the prongs because the field of the permanent magnet 54 field can remain very active. An alternate embodiment can use one hybrid prong and one permanent magnet prong, and still another embodiment can use hybrid prongs having coils interconnected in series on a same circuit, for instance. The hybrid prongs can alternately be as presented in FIG. 8C, for instance.

In an embodiment having two hybrid prongs surrounded by coils 58 connected inversely in series, the coil 58 can be wound in opposite directions such that current 59 applied to IN+ & IN− generates fields that oppose each of the permanent magnet 54 magnetic fields, thus weakening fields of both permanent magnets 54 simultaneously. The number of turns may be different between each prong such that applied current 59 can weaken one permanent magnet prong faster than the other. This strategy can allow one prong to have a reversed field before the other prong's field is turned off. If one permanent magnet prong has more turns than the other, then the current 59 applied to create a field in the reverse direction can cause the field in the permanent magnet 54 with higher turns to reach zero (at −Hci) first before the field in the other permanent magnet 54 (with less turns) does. This unbalance of turns can allow one prong to lose attraction before the other prong does, which can be harnessed to avoid losing a large chip 60 if an alternating sequence is applied such as exemplified above.

Figure 11:
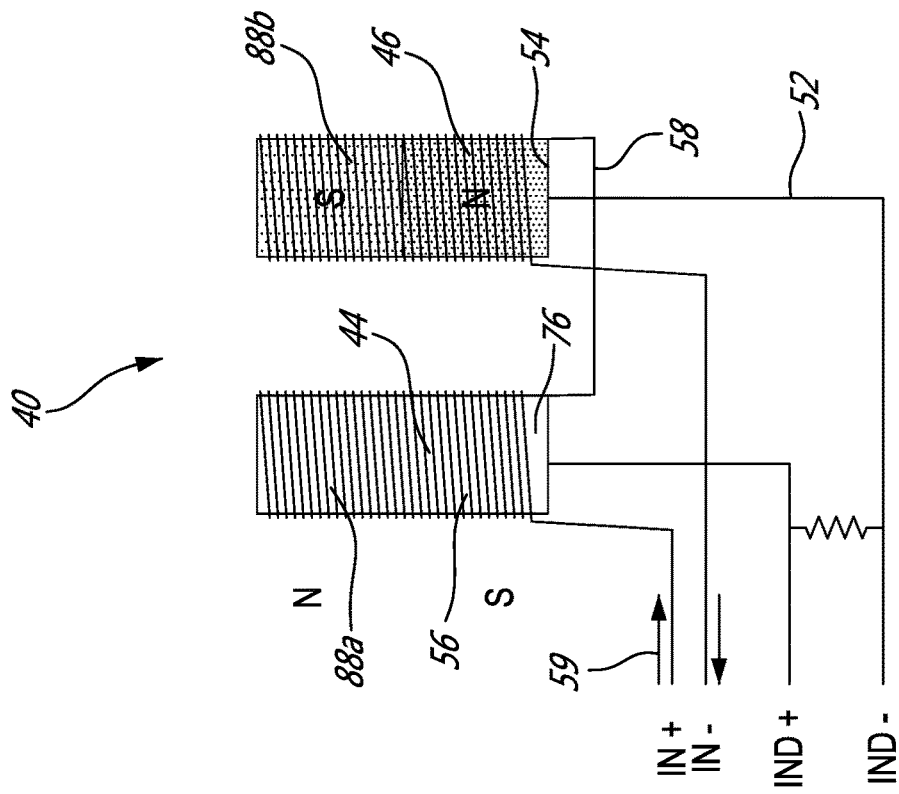
FIG. 11 shows another embodiment of a magnetic chip detector.

A further embodiment is presented in FIG. 11, which can allow example states presented in Table 5, below:

TABLE 5 example states for additional embodiment of FIG. 11

| Function | Probe Current | Probe 1 Field | Probe 2 Field | Effect |
|---|---|---|---|---|
| Chip Detector (Opposite field) | Low Positive | Low N-S | Reduced S-N | Attract chips between prongs. Both fields are low. The EM is low and the PM is reduced. |
| Probe 1 OFF | OFF | Nil or residual N-S | S-N | Chips attracted to probe 2 only. Small chips originally attached to probe 1 fall off. Large chips bridging the gap stay attracted to probe 2. |
| Probe 2 OFF | Positive | N-S | Nil or residual S-N | Chips attracted to probe 1 only. Small chips originally attached to probe 2 fall off. Large chips bridging the gap stay attracted to probe 1. |
| Opposing (Similar field) | Positive+ | High N-S | Low N-S (may demagnetize) | Fields oppose each other. Probe 2 field is lower than probe 1 |

The embodiment of FIG. 11 shows a 4 pin chip detector design with a single coil wrapped around a ferromagnetic core and a permanent magnet in series (or PM in series with ferromagnetic core as shown in FIG. 1 C) to form an electromagnetic prong and an electrically controlled permanent magnet prong, forming an actively controlled chip detector comprised of an electromagnet and a permanent magnet. Both magnetic conductor members (prongs/disks) share a coil wound around each one sequentially to control the magnetic field strength and direction of the electromagnet and to increase, reduce, eliminate or reverse the permanent magnet's field by varying the applied current. The coil can be wound around the ferromagnetic core and the Permanent magnet in such a way that at max current, the electromagnet produces a field opposite of the permanent magnet, while the permanent magnet field is significantly reduced or cancelled. In one operating mode for this chip detector, the current can be applied around half way, such that both the electromagnet and PM have fields opposing each other.

Figure 12:
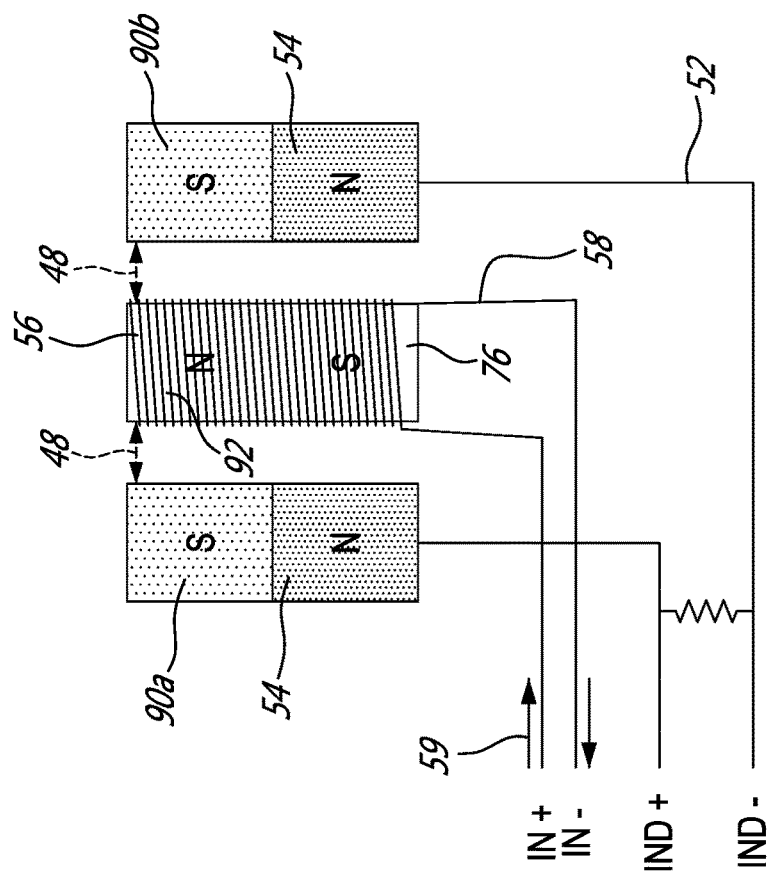
FIG. 12 shows another embodiment of a magnetic chip detector.

A further embodiment is presented in FIG. 12, which can allow example states presented in Table 6, below:

TABLE 6 example states for additional embodiment of FIG. 12

| Function | Probe 2 Current | Probe 1 Field | Probe 2 Field | Probe 3 Field | Effect |
| --- | --- | --- | --- | --- | --- |
| Chip Detector (Opposite field) | Positive | S-N | N-S | S-N | Attract chips between prongs. |
| Probe 2 OFF | OFF | S-N | Nil or residual N-S | S-N | Chips strongly attached to probe 1 & 3, and weakly attached to Probe 2. Large chips bridging the gaps are still attracted because probes 1 & 3 are active. Small chips bridging the gap are shed |
| Opposing (Similar field) | Negative | S-N | S-N | S-N | Small chips bridging the gap repel each other and break the gap |

The embodiment shown in FIG. 12 can be embodied as a 4 pin chip detector design consisting of two permanent magnet prongs 90a, 90b and an electromagnetic prong 92. A single coil 58 wrapped around one ferromagnetic core 76 can be used to form an electromagnetic prong 92. This actively controlled chip detector comprises three magnets: one electromagnet 56 in between and two permanent magnets 54; the electromagnet 56 having a control coil 58 wound around it to control its magnetic field strength and direction by varying the applied current 59. The permanent magnets 54 are electrically connected to a detection circuit 52 that is activated when a chip 60 bridges both gaps 48 between them.

When the electromagnet 56 is activated, it generates a field opposite that of the permanent magnet prongs 92. Similar to traditional chip detectors, a voltage or current is applied to IND+ & IND− and the impedance between these points is measured. As ferromagnetic debris is collected between all three prongs 90a, 90b, 92, the measured impedance will change resulting in a chip 60 indication.

Once the sequence has been exercised once or multiple times, the control system can monitor the resistance again to determine if a chip detection is confirmed. If the resistance is low, it indicates that the collected chip is large and that action should be taken. If the resistance is high, it indicates that the original chips detected were below a certain negligible size. The control system can log both scenarios.

The embodiments described in this document provide non-limiting examples of possible implementations of the present technology. Upon review of the present disclosure, a person of ordinary skill in the art will recognize that changes may be made to the embodiments described herein without departing from the scope of the present technology. For example, the chip detectors can use any suitable conductor member designs (permanent magnet, electro-magnet, permanent electro-magnet) to achieve desired result. The number of conductor member may vary from one embodiment to another, and in particular, a plurality of chip detectors can be used side by side, or otherwise on the same engine. The chip detector system can be used for detecting chips in other liquids than oil or lubricants, such as cooling fluid, for instance. Instead of using two conductor members besides one another, such as in the illustrated examples, alternate embodiments can use two conductor members one around another, for instance. Yet further modifications could be implemented by a person of ordinary skill in the art in view of the present disclosure, which modifications would be within the scope of the present technology.

The invention claimed is:

1. A magnetic chip detector system comprising: a first conductor member and a second conductor member both exposed to a liquid flow path and separated from one another by gap, each one of the conductor members having a magnetic field oriented into the liquid flow path, at least a first one of the magnetic fields being actively modifiable; an electrical energy source configured to induce a current circulation across the gap; and a meter configured to measure a response of the gap to the induced current circulation, the magnetic chip detector system having:
    a first configuration in which a first magnetic field of the first conductor and a second magnetic field of the second conductor have opposite orientations, and
    a second configuration in which the first magnetic field and the second magnetic field have a common orientation.

2. The magnetic chip detector system of claim 1, wherein the gap has a dimension corresponding to a minimum chip size to be detected by the system.

3. The magnetic chip detector system of claim 1, wherein the actively modifiable magnetic field is generated by a coil wrapped around a corresponding conductor member, a controllable electrical energy source being connected to the coil.

4. The magnetic chip detector system of claim 3, wherein the corresponding conductor member is non-magnetized.

5. The magnetic chip detector system of claim 3, wherein the corresponding conductor member has a permanent magnetic field and includes a permanent magnet.

6. The magnetic chip detector system of claim 1, wherein a second one of the magnetic fields is passive and emitted by a permanent magnet forming the corresponding conductor member.

7. The magnetic chip detector system of claim 1, wherein both conductor members having actively modifiable magnetic fields.

8. The magnetic chip detector system of claim 1, further comprising a third conductor member.

9. The magnetic chip detector system of claim 1, further comprising a computer, the computer configured to control the electrical energy source and the at least one actively modifiable magnetic field, read a value resulting from the measurement from the meter and store the read value to a non-transitory memory.

10. A method of monitoring lubricant in an engine, the method comprising:
generating a first magnetic field in a first orientation around at least a first conductor member, the first conductor member and a second conductor member separated from one another by a gap exposed to a flow of the lubricant, the conductor members forming part of an electrical circuit including the lubricant flow area across the gap, and generating a second magnetic field in a second orientation around the second conductor member, the second orientation opposite the first orientation;
inducing an electric current across the circuit, and measuring a first response of the circuit to the induced electric current;
momentarily reversing an orientation of the second magnetic field around the second conductor member from the second orientation to the first orientation such that the first magnetic field and the second magnetic field have a common orientation;
measuring a second response of the circuit to the induced electric current after the momentarily reversing of the orientation of the second magnetic field; and
providing an indication of presence or absence of ferromagnetic chips in the lubricant based on the first and second responses of the circuit.

11. The method of claim 10, comprising increasing a strength of the second magnetic field in the second orientation after the momentarily reversing of the orientation to pull a ferromagnetic chip into contact with the second conductor member, thereby closing the circuit and allowing current circulation across it, said step of providing an indication including providing an indication of a presence of ferromagnetic chips in the lubricant.

12. The method of claim 11, wherein the step of generating the first magnetic field in the first orientation includes establishing an absence of magnetic field around the second conductor member prior to the increasing of the strength of the second magnetic field around the second conductor member.

13. The method of claim 12, further comprising subsequently to the increasing of the strength in the second orientation, controlling the magnetic field around the first conductor member as follows: reducing the strength of the second magnetic field, reversing its orientation, increasing its strength in the second orientation, reducing its strength, reversing its orientation, and increasing its strength in the first orientation.

14. The method of claim 10, comprising repeating the momentarily reversing of the orientation of the second magnetic field.

15. The method of claim 14, wherein the repeating includes applying a sinusoidal electric current to a coil surrounding the second conductor member.

16. The method of claim 10, wherein the second conductor member is a permanent magnet generating an intrinsic magnetic field in the second orientation and wrapped by a coil, and wherein the generating of the second magnetic field in the second orientation around the second conductor member includes circulating current in the coil in a manner to reduce, cancel out, or reverse the intrinsic magnetic field of the permanent magnet.

17. The method of claim 10, comprising reducing the strength of the second magnetic field around the second conductor member and thereby ridding the first and second conductor members of chips below a threshold size, the providing of the indication includes providing an indication of presence of ferromagnetic chips in the lubricant upon measuring a response including detecting current circulation above a threshold after the momentarily reversing of the orientation of the second magnetic field.

18. The method of claim 17, wherein the step of reducing is contingent upon said measuring a response including detecting current circulation above the threshold.

19. The method of claim 10, wherein said step of inducing an electrical current includes applying a difference of potential across the first and second conductor members, and the measuring of the first current and of the second current includes obtaining a measurement indicative of current circulation amplitude across the first and second conductor members in response to the difference of potential.

* * * * *